(12) United States Patent
O'Neil et al.

(10) Patent No.: US 9,226,764 B2
(45) Date of Patent: Jan. 5, 2016

(54) CONFORMABLE SOFT TISSUE REMOVAL INSTRUMENTS

(75) Inventors: Michael J. O'Neil, Raynham, MA (US); Jonathan Bellas, Raynham, MA (US); John Riley Hawkins, Raynham, MA (US); Cody Cranson, Raynham, MA (US); Christopher Ramsay, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 537 days.

(21) Appl. No.: 13/413,282

(22) Filed: Mar. 6, 2012

(65) Prior Publication Data

US 2013/0238006 A1 Sep. 12, 2013

(51) Int. Cl.
*A61B 17/32* (2006.01)
*A61B 17/3207* (2006.01)
*A61B 17/00* (2006.01)
*A61B 17/29* (2006.01)

(52) U.S. Cl.
CPC .......... *A61B 17/32* (2013.01); *A61B 17/320016* (2013.01); *A61B 17/320708* (2013.01); *A61B 2017/00261* (2013.01); *A61B 2017/00473* (2013.01); *A61B 2017/2927* (2013.01); *A61B 2017/320008* (2013.01)

(58) Field of Classification Search
CPC ............... A61B 17/1659; A61B 17/32; A61B 17/320708; A61B 2017/320004; A61B 2017/320008
USPC .......... 606/79, 84, 160, 167, 170; 30/169–172
See application file for complete search history.

(56) References Cited

U.S. PATENT DOCUMENTS

| | | | |
|---|---|---|---|
| 4,105,034 A | 8/1978 | Shalaby | |
| 4,130,639 A | 12/1978 | Shalaby | |
| 4,140,678 A | 2/1979 | Shalaby | |
| 4,141,087 A | 2/1979 | Shalaby | |
| 4,205,399 A | 6/1980 | Shalaby | |
| 4,208,511 A | 6/1980 | Shalaby | |
| 4,538,612 A * | 9/1985 | Patrick, Jr. | ..................... 606/131 |
| 4,834,757 A | 5/1989 | Brantigan | |
| 5,006,121 A | 4/1991 | Hafeli | |

(Continued)

FOREIGN PATENT DOCUMENTS

| | | |
|---|---|---|
| DE | 10357960 | 7/2005 |
| EP | 609084 | 9/1997 |
| EP | 1283026 | 9/2003 |
| EP | 1405602 | 4/2004 |
| EP | 1605836 | 12/2005 |
| EP | 1308132 | 12/2006 |
| EP | 1829486 | 9/2007 |
| FR | 2874814 | 11/2007 |

(Continued)

OTHER PUBLICATIONS

U.S. Appl. No. 61/009,546, filed on Dec. 28, 2007 Rodgers.
U.S. Appl. No. 61/140,926, filed on Dec. 26, 2008 Spann.
U.S. Appl. No. 61/178,315, filed on May 14, 2009 Spann.

(Continued)

*Primary Examiner* — Christian Sevilla
*Assistant Examiner* — Eric S Gibson

(57) ABSTRACT

Surgical curettes or rakes with cutting edges conform or deflect to allow for contouring that follows the bony anatomy. The cutting tips can be pre-sterile, disposable and made from flexible materials including metals and polymers. The disposable tips ensure that a sharp cutting edge is exposed to the endplate for each procedure. The tips can also be adjusted to change the size of the cutting surface and window for retaining shaved disc material. The tips can pivot to provide for a self adjusting angle that allows the cutting edge to have full contact with the endplate at various angles like the pivot on a disposable razor blade.

22 Claims, 7 Drawing Sheets

(56) References Cited

U.S. PATENT DOCUMENTS

| Patent No. | | Date | Inventor | Cite |
|---|---|---|---|---|
| 5,019,082 | A | 5/1991 | Frey | |
| 5,133,719 | A | 7/1992 | Winston | |
| 5,163,939 | A | 11/1992 | Winston | |
| 5,169,402 | A | 12/1992 | Elloy | |
| 5,171,278 | A | 12/1992 | Pisharodi | |
| 5,217,475 | A * | 6/1993 | Kuber | 606/161 |
| 5,250,061 | A | 10/1993 | Michelson | |
| 5,320,644 | A | 6/1994 | Baumgartner | |
| 5,342,365 | A | 8/1994 | Waldman | |
| 5,387,215 | A | 2/1995 | Fisher | |
| 5,390,683 | A | 2/1995 | Pisharodi | |
| 5,454,815 | A | 10/1995 | Geisser | |
| 5,454,827 | A | 10/1995 | Aust | |
| 5,464,929 | A | 11/1995 | Bezwada | |
| 5,522,899 | A | 6/1996 | Michelson | |
| 5,540,693 | A | 7/1996 | Fisher | |
| 5,595,751 | A | 1/1997 | Bezwada | |
| 5,597,579 | A | 1/1997 | Bezwada | |
| 5,601,561 | A | 2/1997 | Terry | |
| 5,607,687 | A | 3/1997 | Bezwada | |
| 5,618,552 | A | 4/1997 | Bezwada | |
| 5,620,698 | A | 4/1997 | Bezwada | |
| 5,645,850 | A | 7/1997 | Bezwada | |
| 5,648,088 | A | 7/1997 | Bezwada | |
| 5,658,335 | A | 8/1997 | Allen | |
| 5,665,122 | A | 9/1997 | Kambin | |
| 5,693,100 | A | 12/1997 | Pisharodi | |
| 5,698,213 | A | 12/1997 | Jamiolkowski | |
| 5,700,583 | A | 12/1997 | Jamiolkowski | |
| 5,725,531 | A | 3/1998 | Shapiro | |
| 5,857,995 | A | 1/1999 | Thomas | |
| 5,859,150 | A | 1/1999 | Jamiolkowski | |
| 5,916,228 | A * | 6/1999 | Ripich et al. | 606/161 |
| 5,925,056 | A | 7/1999 | Thomas | |
| 5,976,187 | A | 11/1999 | Richelsoph | |
| 5,980,522 | A | 11/1999 | Koros | |
| 6,039,761 | A | 3/2000 | Li | |
| 6,045,579 | A | 4/2000 | Hochshuler et al. | |
| 6,053,922 | A | 4/2000 | Krause | |
| 6,056,763 | A * | 5/2000 | Parsons | 606/161 |
| 6,080,158 | A | 6/2000 | Lin | |
| 6,106,557 | A | 8/2000 | Robioneck | |
| 6,120,508 | A | 9/2000 | Grunig | |
| 6,126,689 | A | 10/2000 | Brett | |
| 6,139,558 | A * | 10/2000 | Wagner | 606/161 |
| 6,251,140 | B1 | 6/2001 | Marino | |
| 6,258,093 | B1 | 7/2001 | Edwards | |
| 6,296,644 | B1 | 10/2001 | Saurat | |
| D450,676 | S * | 11/2001 | Huttner | D24/147 |
| 6,342,074 | B1 | 1/2002 | Simpson | |
| 6,387,130 | B1 | 5/2002 | Stone | |
| 6,398,793 | B1 * | 6/2002 | McGuire | 606/131 |
| 6,409,766 | B1 | 6/2002 | Brett | |
| 6,436,101 | B1 | 8/2002 | Hamada | |
| 6,447,518 | B1 | 9/2002 | Krause | |
| 6,610,066 | B2 | 8/2003 | Dinger | |
| 6,635,060 | B2 | 10/2003 | Hanson | |
| RE38,335 | E | 11/2003 | Aust | |
| 6,641,582 | B1 | 11/2003 | Hanson | |
| 6,660,004 | B2 | 12/2003 | Barker | |
| 6,755,837 | B2 | 6/2004 | Ebner | |
| 6,764,491 | B2 | 7/2004 | Frey | |
| 6,840,941 | B2 | 1/2005 | Rogers | |
| 6,878,167 | B2 | 4/2005 | Ferree | |
| 6,949,108 | B2 * | 9/2005 | Holmes | 606/160 |
| 6,966,912 | B2 | 11/2005 | Michelson | |
| 7,018,415 | B1 | 3/2006 | McKay | |
| 7,060,073 | B2 | 6/2006 | Frey | |
| 7,070,598 | B2 | 7/2006 | Lim | |
| 7,087,055 | B2 | 8/2006 | Lim | |
| 7,125,424 | B2 | 10/2006 | Banick | |
| 7,226,482 | B2 | 6/2007 | Messerli | |
| 7,351,262 | B2 | 4/2008 | Bindseil | |
| 7,470,273 | B2 | 12/2008 | Dougherty-Shah | |
| 7,491,237 | B2 | 2/2009 | Randall | |
| 7,572,279 | B2 | 8/2009 | Jackson | |
| 7,575,580 | B2 | 8/2009 | Lim | |
| 7,578,820 | B2 | 8/2009 | Moore | |
| 7,601,173 | B2 | 10/2009 | Messerli | |
| 7,618,458 | B2 | 11/2009 | Biedermann | |
| 7,625,377 | B2 | 12/2009 | Veldhuizen | |
| 7,625,394 | B2 | 12/2009 | Molz, IV | |
| 7,666,186 | B2 | 2/2010 | Harp | |
| 7,674,265 | B2 | 3/2010 | Smith | |
| 7,682,400 | B2 | 3/2010 | Zwirkoski | |
| 7,803,161 | B2 | 9/2010 | Foley | |
| 7,828,849 | B2 | 11/2010 | Lim | |
| 7,918,874 | B2 | 4/2011 | Siegal | |
| 7,922,719 | B2 * | 4/2011 | Ralph et al. | 606/79 |
| 7,938,857 | B2 | 5/2011 | Garcia-Bengochea | |
| 8,012,212 | B2 | 9/2011 | Link | |
| 8,025,697 | B2 | 9/2011 | McClellan, III | |
| 8,038,703 | B2 | 10/2011 | Dobak, III | |
| 8,043,293 | B2 | 10/2011 | Warnick | |
| 8,128,700 | B2 | 3/2012 | Delurio | |
| 8,216,317 | B2 | 7/2012 | Thibodeau | |
| 8,241,364 | B2 | 8/2012 | Hansell | |
| 8,343,222 | B2 | 1/2013 | Cope | |
| 8,529,568 | B2 * | 9/2013 | Bouadi | 606/84 |
| 8,579,981 | B2 | 11/2013 | Lim | |
| 8,628,577 | B1 | 1/2014 | Jimenez | |
| 8,663,331 | B2 | 3/2014 | McClellan, III | |
| 8,845,733 | B2 | 9/2014 | O'Neil | |
| 8,920,506 | B2 | 12/2014 | McGuckin, Jr. | |
| 8,940,050 | B2 | 1/2015 | Laurence | |
| 2002/0138078 | A1 | 9/2002 | Chappuis | |
| 2002/0165550 | A1 | 11/2002 | Frey | |
| 2002/0183758 | A1 | 12/2002 | Middleton | |
| 2003/0135275 | A1 | 7/2003 | Garcia | |
| 2003/0191531 | A1 | 10/2003 | Berry | |
| 2004/0030387 | A1 | 2/2004 | Landry | |
| 2004/0059337 | A1 | 3/2004 | Hanson | |
| 2004/0068269 | A1 | 4/2004 | Bonati | |
| 2004/0083000 | A1 | 4/2004 | Keller | |
| 2004/0102784 | A1 | 5/2004 | Pasquet | |
| 2004/0102846 | A1 | 5/2004 | Keller | |
| 2004/0127990 | A1 | 7/2004 | Bartish | |
| 2004/0147129 | A1 | 7/2004 | Rolfson | |
| 2004/0220668 | A1 | 11/2004 | Eisermann | |
| 2005/0038431 | A1 | 2/2005 | Bartish | |
| 2005/0096745 | A1 | 5/2005 | Andre | |
| 2005/0149034 | A1 * | 7/2005 | Assell et al. | 606/79 |
| 2005/0165420 | A1 | 7/2005 | Cha | |
| 2005/0171541 | A1 | 8/2005 | Boehm | |
| 2005/0177173 | A1 | 8/2005 | Aebi | |
| 2005/0240193 | A1 | 10/2005 | Layne | |
| 2006/0036244 | A1 | 2/2006 | Spitler | |
| 2006/0058807 | A1 | 3/2006 | Landry | |
| 2006/0064101 | A1 | 3/2006 | Arramon | |
| 2006/0064102 | A1 | 3/2006 | Ebner | |
| 2006/0069436 | A1 | 3/2006 | Sutton | |
| 2006/0074429 | A1 * | 4/2006 | Ralph et al. | 606/84 |
| 2006/0100622 | A1 | 5/2006 | Jackson | |
| 2006/0111715 | A1 | 5/2006 | Jackson | |
| 2006/0111728 | A1 | 5/2006 | Abdou | |
| 2006/0129244 | A1 | 6/2006 | Ensign | |
| 2006/0142858 | A1 | 6/2006 | Colleran | |
| 2006/0167547 | A1 | 7/2006 | Suddaby | |
| 2006/0189999 | A1 | 8/2006 | Zwirkoski | |
| 2006/0212118 | A1 | 9/2006 | Abernathie | |
| 2006/0229627 | A1 | 10/2006 | Hunt | |
| 2006/0235426 | A1 | 10/2006 | Lim | |
| 2006/0253120 | A1 | 11/2006 | Anderson | |
| 2006/0254784 | A1 | 11/2006 | Hartmann et al. | |
| 2006/0265077 | A1 | 11/2006 | Zwirkoski | |
| 2006/0293753 | A1 | 12/2006 | Thramann | |
| 2007/0055264 | A1 | 3/2007 | Parmigiani | |
| 2007/0067035 | A1 | 3/2007 | Falahee | |
| 2007/0093897 | A1 | 4/2007 | Gerbec | |
| 2007/0142843 | A1 | 6/2007 | Dye | |
| 2007/0162132 | A1 | 7/2007 | Messerli | |
| 2007/0213737 | A1 | 9/2007 | Schermerhorn | |
| 2007/0213826 | A1 | 9/2007 | Smith | |
| 2007/0225726 | A1 | 9/2007 | Dye | |

(56) References Cited

U.S. PATENT DOCUMENTS

| | | |
|---|---|---|
| 2007/0225815 A1 | 9/2007 | Keith |
| 2007/0233130 A1 | 10/2007 | Suddaby |
| 2007/0260314 A1 | 11/2007 | Biyani |
| 2007/0270957 A1 | 11/2007 | Heinz |
| 2007/0270968 A1 | 11/2007 | Baynham |
| 2008/0027544 A1 | 1/2008 | Melkent |
| 2008/0027550 A1 | 1/2008 | Link |
| 2008/0045966 A1 | 2/2008 | Buttermann |
| 2008/0051890 A1 | 2/2008 | Waugh |
| 2008/0058933 A1 | 3/2008 | Garner |
| 2008/0065082 A1 | 3/2008 | Chang |
| 2008/0077150 A1 | 3/2008 | Nguyen |
| 2008/0077241 A1 | 3/2008 | Nguyen |
| 2008/0082173 A1 | 4/2008 | Delurio |
| 2008/0091211 A1 | 4/2008 | Gately |
| 2008/0097454 A1 | 4/2008 | DeRidder |
| 2008/0108990 A1 | 5/2008 | Mitchell |
| 2008/0119935 A1 | 5/2008 | Alvarez |
| 2008/0125865 A1 | 5/2008 | Abdelgany |
| 2008/0133012 A1 | 6/2008 | McGuckin |
| 2008/0140085 A1 | 6/2008 | Gately |
| 2008/0154379 A1 | 6/2008 | Steiner |
| 2008/0208255 A1 | 8/2008 | Siegal |
| 2008/0221586 A1 | 9/2008 | Garcia-Bengochea |
| 2008/0221687 A1 | 9/2008 | Viker |
| 2008/0234732 A1 | 9/2008 | Landry |
| 2008/0234733 A1 | 9/2008 | Scrantz |
| 2008/0243126 A1 | 10/2008 | Gutierrez |
| 2008/0243255 A1 | 10/2008 | Butler |
| 2008/0249628 A1 | 10/2008 | Altarac |
| 2008/0255563 A1 | 10/2008 | Farr |
| 2008/0255574 A1 | 10/2008 | Dye |
| 2008/0269904 A1 | 10/2008 | Voorhies |
| 2008/0312743 A1 | 12/2008 | Vila |
| 2009/0030423 A1 | 1/2009 | Puno |
| 2009/0054898 A1 | 2/2009 | Gleason |
| 2009/0054911 A1 | 2/2009 | Mueller |
| 2009/0062807 A1 | 3/2009 | Song |
| 2009/0076607 A1 | 3/2009 | Aalsma |
| 2009/0112217 A1 | 4/2009 | Hester |
| 2009/0143859 A1 | 6/2009 | McClellan, III |
| 2009/0182431 A1 | 7/2009 | Butler |
| 2009/0192616 A1 | 7/2009 | Zielinski |
| 2009/0216234 A1 | 8/2009 | Farr |
| 2009/0234364 A1 | 9/2009 | Crook |
| 2009/0240335 A1 | 9/2009 | Arcenio |
| 2009/0276049 A1 | 11/2009 | Weiland |
| 2009/0299479 A1 | 12/2009 | Jones |
| 2010/0016968 A1 | 1/2010 | Moore |
| 2010/0030217 A1 | 2/2010 | Mitusina |
| 2010/0076502 A1 | 3/2010 | Guyer |
| 2010/0094422 A1 | 4/2010 | Hansell |
| 2010/0100098 A1 | 4/2010 | Norton |
| 2010/0125334 A1 | 5/2010 | Krueger |
| 2010/0161060 A1 | 6/2010 | Schaller |
| 2010/0174321 A1 | 7/2010 | Schaller |
| 2010/0185290 A1 | 7/2010 | Compton |
| 2010/0191241 A1 | 7/2010 | McCormack |
| 2010/0198263 A1 | 8/2010 | Siegal |
| 2010/0211076 A1 | 8/2010 | Germain |
| 2010/0211107 A1 | 8/2010 | Muhanna |
| 2010/0217269 A1 | 8/2010 | Landes |
| 2010/0234849 A1* | 9/2010 | Bouadi ............................ 606/84 |
| 2010/0249935 A1 | 9/2010 | Slivka |
| 2010/0256768 A1 | 10/2010 | Lim |
| 2010/0280619 A1 | 11/2010 | Yuan |
| 2010/0305700 A1 | 12/2010 | Ben-Arye |
| 2010/0305704 A1 | 12/2010 | Messerli |
| 2010/0331845 A1 | 12/2010 | Foley |
| 2011/0004216 A1 | 1/2011 | Amendola |
| 2011/0009970 A1 | 1/2011 | Puno |
| 2011/0029083 A1 | 2/2011 | Hynes |
| 2011/0029085 A1 | 2/2011 | Hynes |
| 2011/0035011 A1 | 2/2011 | Cain |
| 2011/0106260 A1 | 5/2011 | Laurence |
| 2011/0112586 A1 | 5/2011 | Guyer |
| 2011/0125266 A1 | 5/2011 | Rodgers |
| 2011/0276142 A1 | 11/2011 | Niemiec |
| 2011/0282459 A1 | 11/2011 | McClellan, III |
| 2011/0301712 A1 | 12/2011 | Palmatier et al. |
| 2011/0319898 A1 | 12/2011 | O'Neil |
| 2011/0319899 A1* | 12/2011 | O'Neil et al. ................... 606/84 |
| 2011/0319998 A1 | 12/2011 | O'Neil |
| 2011/0319999 A1 | 12/2011 | O'Neil |
| 2011/0320000 A1 | 12/2011 | O'Neil |
| 2012/0035730 A1 | 2/2012 | Spann |
| 2012/0209383 A1 | 8/2012 | Tsuang |
| 2012/0277877 A1 | 11/2012 | Smith |
| 2013/0006362 A1 | 1/2013 | Biedermann |
| 2013/0023937 A1 | 1/2013 | Biedermann |
| 2013/0035762 A1 | 2/2013 | Siegal |
| 2013/0109925 A1 | 5/2013 | Horton |
| 2013/0116791 A1 | 5/2013 | Theofilos |
| 2013/0138214 A1 | 5/2013 | Greenhalgh |
| 2013/0150906 A1 | 6/2013 | Kerboul |
| 2013/0173004 A1 | 7/2013 | Greenhalgh |
| 2013/0238006 A1* | 9/2013 | O'Neil et al. ................. 606/170 |
| 2013/0268077 A1 | 10/2013 | You |
| 2013/0310937 A1 | 11/2013 | Pimenta |
| 2014/0025170 A1 | 1/2014 | Lim |
| 2014/0039626 A1 | 2/2014 | Mitchell |
| 2014/0058512 A1 | 2/2014 | Petersheim |
| 2014/0058513 A1 | 2/2014 | Gahman |
| 2014/0172103 A1 | 6/2014 | O'Neil |
| 2014/0172105 A1 | 6/2014 | Frasier |

FOREIGN PATENT DOCUMENTS

| | | |
|---|---|---|
| FR | 2948277 | 11/2012 |
| WO | WO 9214423 | 9/1992 |
| WO | WO 9834568 | 8/1998 |
| WO | 9963914 | 12/1999 |
| WO | WO 9960956 | 12/1999 |
| WO | 0024343 | 5/2000 |
| WO | WO 0203870 | 1/2002 |
| WO | WO 03003951 | 1/2003 |
| WO | WO 2004080316 | 9/2004 |
| WO | WO 2006072941 | 7/2006 |
| WO | 2006118944 | 11/2006 |
| WO | 2006044920 | 12/2006 |
| WO | WO 2008005627 | 1/2008 |
| WO | WO 2010011348 | 1/2010 |
| WO | WO 2010075555 | 10/2010 |
| WO | WO 2010121002 | 12/2010 |
| WO | WO 2011060087 | 5/2011 |
| WO | WO 2012027490 | 3/2012 |
| WO | WO 2012103254 | 8/2012 |
| WO | 2012129197 | 9/2012 |
| WO | 2013149611 | 10/2013 |

OTHER PUBLICATIONS

Vandorpe, "Biodegradable Polyphosphazenes for Biomedical Applications"; *Handbook of Biodegradable Polymers*; 1997; pp. 161-182; Hardwood Academic Press.

Allcock, "Polyphosphazenes"; *The Encyclopedia of Polymer Science*; 1988; pp. 31-41; vol. 13; Wiley Intersciences, John Wiley & Sons.

Cohn, "Polymer Preprints"; *Journal of Biomaterials Research*; 1989; p. 498; Biomaterials Research Labortatory, Casali Institute of Applied Chemistry, Israel.

Cohn, "Biodegradable PEO/PLA Block Copolymers"; *Journal of Biomedical Materials Research*; 1988; pp. 993-1009; vol. 22; John Wiley & Sons, Inc.

Heller, "Poly (Otrho Esters)"; *Handbook of Biodegradable Polymers*; edited by Domb; et al; Hardwood Academic Press; 1997; pp. 99-118.

Kemnitzer, "Degradable Polymers Derived From the Amino Acid L-Tyrosine"; 1997; pp. 251-272; edited by Domb, et. al., Hardwood Academic Press.

Khoo, Axilif address spongy from the caudal approach. Minimally Invasive Correction of Grage I and II Isthmic Spondylolisthesis using AsiaLiF for L5/S1 Fusion, pp. 45/0123 Rev B Sep. 15, 2008.

\* cited by examiner

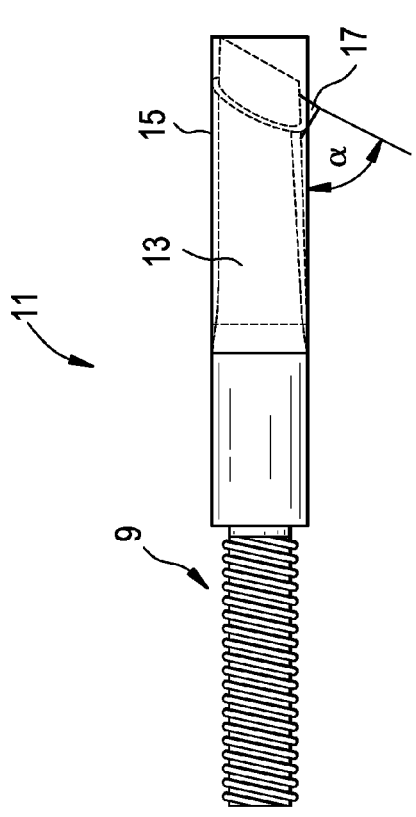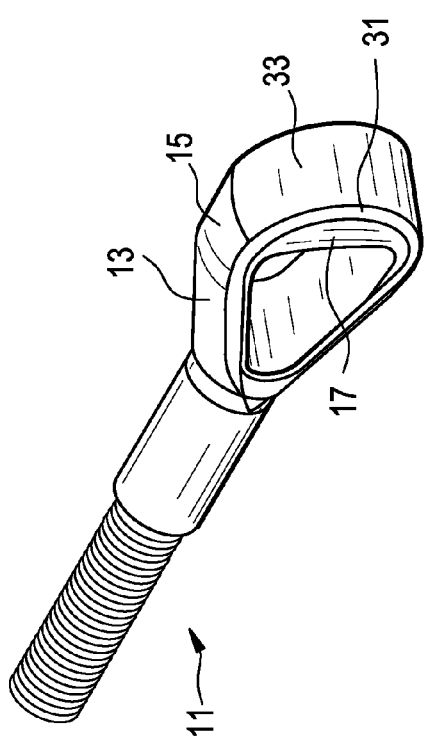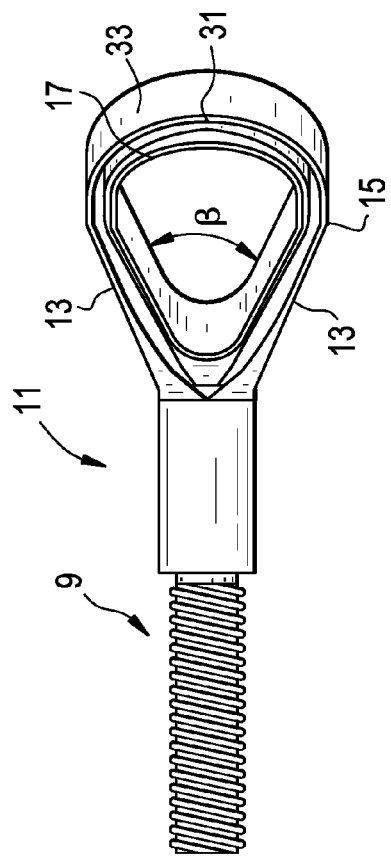

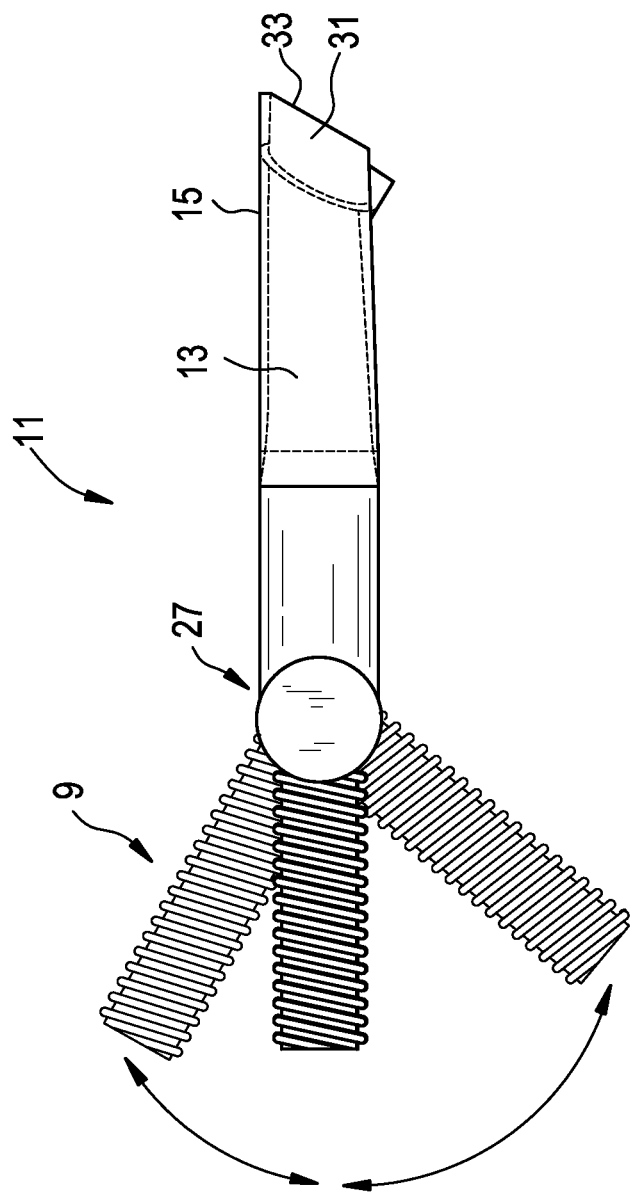

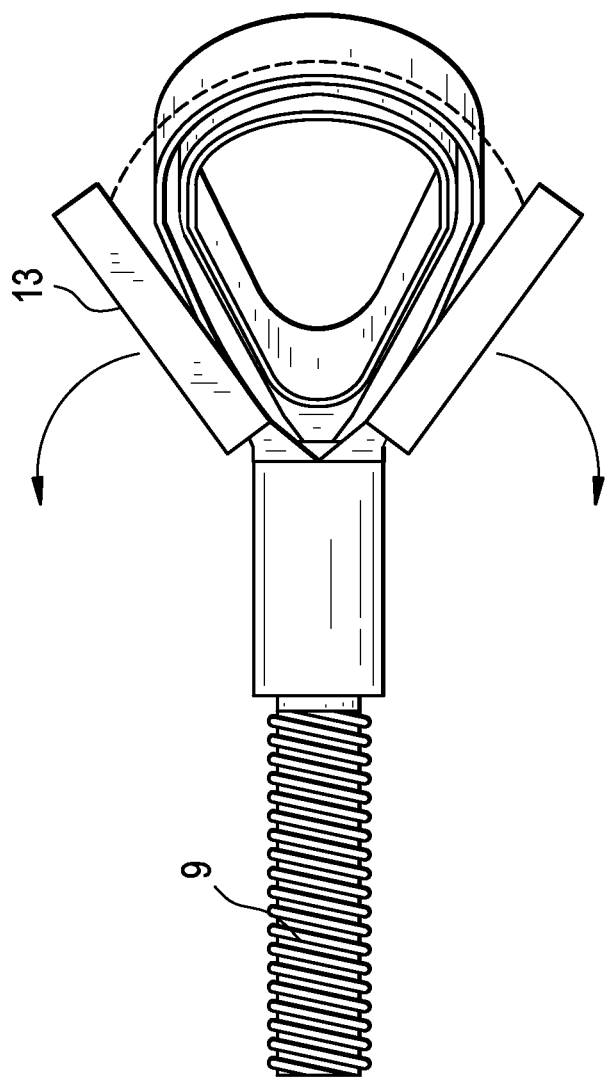

CONFORMABLE SOFT TISSUE REMOVAL INSTRUMENTS

BACKGROUND OF THE INVENTION

Soft tissue removal from bony structures is often required in various surgical procedures. For example, in a discectomy, selected portions of the intervertebral disc must be cleared to create a disc space between adjacent vertebrae. Underlying bony tissue damage incurred with current surgical site preparation instruments and surgical techniques can lead to a host of issues, including excessive or inadequate tissue removal, improper spinal correction, device subsidence, and may even prompt revision surgery. Current disc clearing instruments do not conform to the anatomy and often form undesired grooves or channel in the anatomy. In addition, they also require periodic maintenance to ensure their continued sharpness, and must be cleaned and sterilized after each use.

In addition, soft tissue (such as a disc) selected for removal in orthopedic surgery is often located in a position that is blinded to the surgeon.

US Patent Publication No. 2007-0233130 (Suddaby) discloses tool for preparing vertebral surfaces following a discectomy has a body and a rotary cutting tool mounted at the distal end of a lever which extends through the body. The proximal end of the lever can be squeezed toward the body to force the cutting tool against the vertebral surface facing it, while the tool is rotated by turning a crank supported on the tool body, or by a motor. The cutting tool is preferably a flexible rasp or blade which can conform to and control the convexity of the prepared surface.

U.S. Pat. No. 5,454,827 (Re. 38,335) (Aust) discloses a surgical instrument includes a handle, a first stem section having a longitudinal axis and extending from the handle, and a tissue engaging member for engaging tissue. A second stem section, connected between the first stem section and the tissue engaging member, has a portion which is bendable and supports the tissue engaging member for movement between a plurality of orientations relative to the axis and to the first stem section. The surgical instrument includes a system for bending the bendable portion of the second stem section to change the orientation of the tissue engaging member relative to the axis and to the first stem section from a first orientation to a second orientation. The bendable portion of the second stem section includes a member for enabling bending movement of the bendable portion to locate the tissue engaging member at the same angle relative to the longitudinal axis of the first stem section at more than one location along the length of the bendable portion. The marketed version of this flexible shaver claims to minimize endplate damage.

SUMMARY OF THE INVENTION

The present inventors have recognized a need to create an easy to use, versatile, consistent tissue removal instrument that can reduce time in surgery and decrease patient exposure to pathogens. The present inventors have further recognized that a blade that accommodates unseen variations in bony anatomy would improve the safety of the cut.

In accordance with these goals, the present inventors have developed surgical shaving instruments with cutting tips that conform or deflect to allow for contouring that follows the bony anatomy. The cutting tips can be pre-sterile and disposable, and its blade may be made from flexible materials including metals and polymers. The disposable nature of the cutting tip ensures that a sharp cutting edge on the blade is exposed to the endplate in each surgical procedure. The tips can also be adjusted to change the size of the cutting surface and the window for retaining shaved disc material. The cutting tip can be made to pivot to provide for a self-adjusting angle that allows the blade to have full contact with the endplate at various angles (in a manner similar to a pivot on a conventional disposable razor blade). It is believed that a conformable blade reduces the likelihood of endplate damage by increasing the contact area of the cutting edge of the blade with the endplate, as well as following bony anatomy. Conformable blades may also increase the ability to remove disc material from the endplate with less effort and fewer insertions into the disc space when compared to a conventional rigid curette or rake. By reducing the number of insertions, the chances of damaging a nerve may decrease as well. Flexing prevents incurring damage beyond the endplate into the cortical bone while allowing removal of cartilaginous tissue attached to the endplate.

Therefore, in accordance with the present invention, there is provided an instrument for removing soft tissue, comprising;
  a) a shaft having a proximal end portion and a distal end portion,
  b) a cutting tip attached to the distal end portion of the shaft, the tip comprising:
    i) a proximal end portion adapted to attach to the shaft, and
    ii) distal end portion comprising:
      first and second tynes extending distally from the proximal end portion of the cutting tip, each tyne having a distal end portion, and
      a flexible blade connected to each of the distal end portions of the tynes,
wherein the blade is adapted to flex in response to a conventional level of force used by a spinal surgeon in shaving cartilaginous tissue from an endplate of a disc space with a curette.

DESCRIPTION OF THE FIGURES

FIGS. 2a-2c disclose various views of a preferred cutting tip of the present invention.

FIG. 4 discloses an embodiment of the cutting tip of the present invention having a pivot.

FIG. 5 discloses an embodiment of the cutting tip of the present invention having flexible tynes.

DETAILED DESCRIPTION OF THE INVENTION

Figure 1:
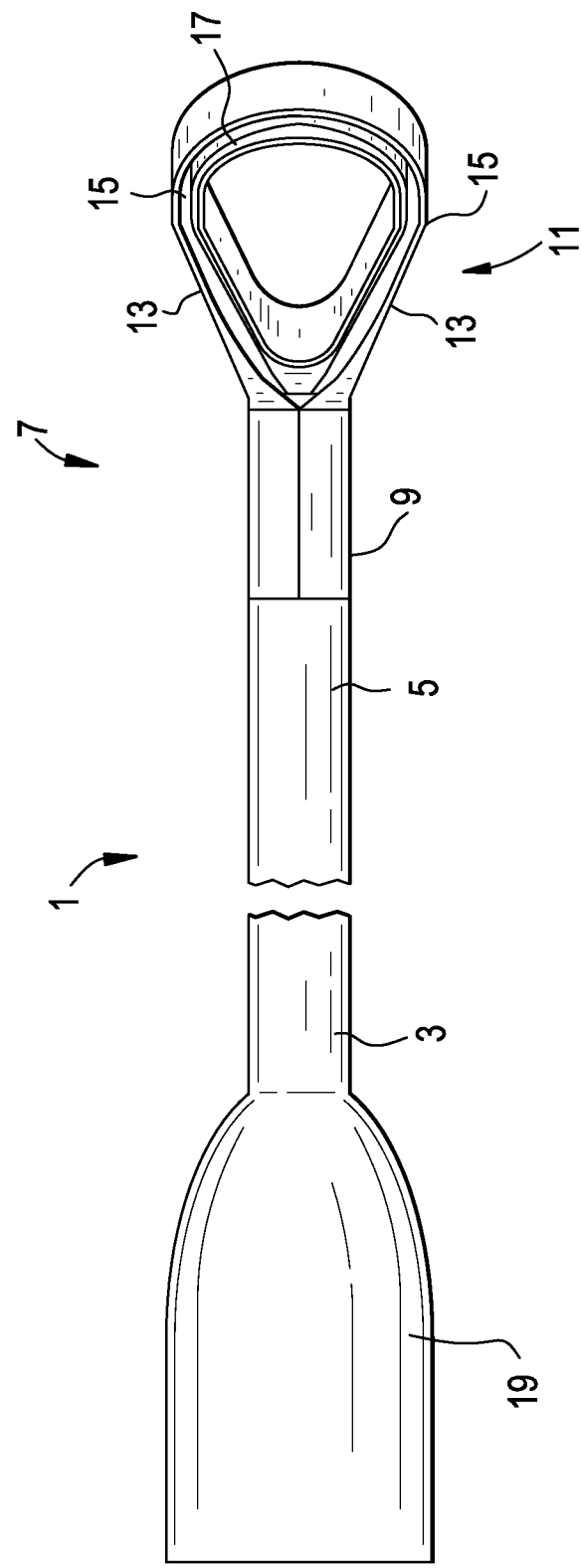
FIG. 1 is a bottom view of the shaving instrument of the present invention.

For the purposes of the present invention, the terms "shaver" and "curette" are used interchangeably.

For the purposes of the present invention, a "flexible" blade flexes in response to a conventional level of force used by a spinal surgeon in shaving cartilaginous tissue from an endplate of a disc space with a curette.

Now referring to FIGS. 1, and 2a-2c, there is provided an instrument for removing soft tissue, comprising;
  a) a shaft 1 having a proximal end portion 3 and a distal end portion 5,
  b) a cutting tip 7 attached to the distal end portion of the shaft, the tip comprising:

i) a proximal end portion 9 adapted to attach to the shaft, and ii) a distal end portion 11 comprising:
first and second tynes 13 extending distally from the proximal end portion of the cutting tip, each tyne having a distal end portion 15, and
a flexible blade 17 connected to each of the distal end portions of the tynes.

In some embodiments, the proximal end portion of the shaft forms a handle 19. The handle allows for easy manipulation of the instrument by the surgeon.

Figure 3A:
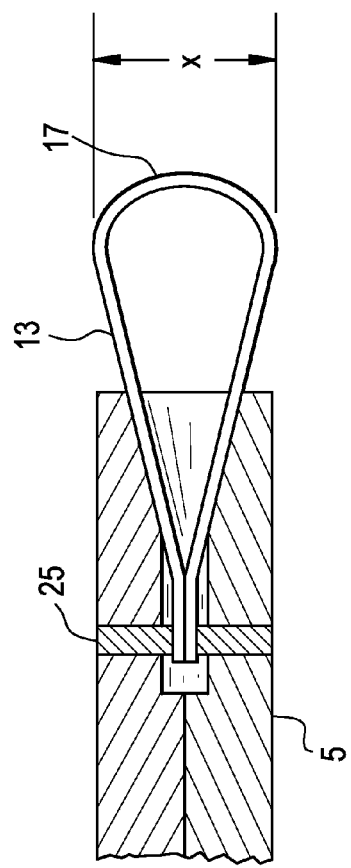
FIGS. 3a-3b disclose two modular shavers of the present invention.
Figure 3B:
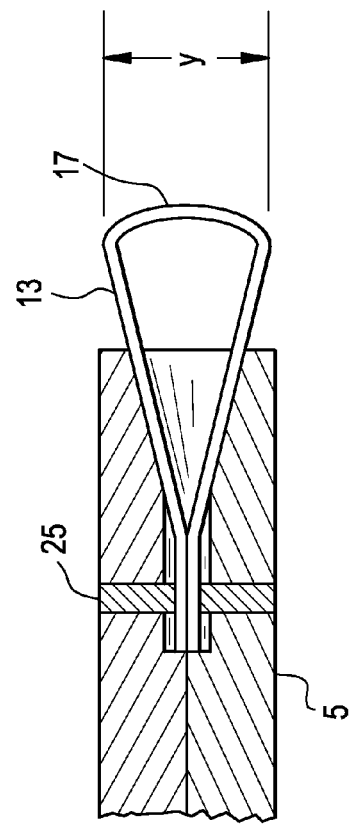

In some embodiments, the distal end portion of the shaft and the proximal end portion of the cutting tip are modular. This modularity allows the surgeon to select the appropriate size, shape and stiffness of the cutting tip for a particular case. It also allows the number of shafts in the instrument tray to be reduced. In preferred embodiments thereof, the distal end portion of the shaft and the proximal end portion of the cutting tip are threadably mated, thereby providing a simple method of changing tips. Other modes of removably mating the shaft and tip may include snap, Hudson, and key attachments. FIG. 2c shows the cutting tip having a threaded proximal end portion. In some embodiments, the blade is press-fit into the convex support 33. In other embodiments, and now referring to FIGS. 3a and 3b, the distal end portion of the shaft has a first throughhole, the proximal end portion of the cutting tip has a second throughhole, and a connecting pin 25 passes through each throughhole. This mode of connection has the advantage of providing quick and easy interchangeability, modularity and tension adjustability. Also in FIGS. 3a and 3b, the blade and tynes are represented by a single integral piece of flexible metal.

In other embodiments, the distal end portion of the shaft and the proximal end portion of the cutting tip are integral. The integral connection is advantageously simple to sterilize.

In some embodiments, and now referring to FIG. 4, the cutting tip further comprises a pivot 27 located between its proximal end portion and its distal end portion. The pivot accommodates various angles of entry into the disc space. In some embodiments thereof, the tynes form a plane, and the pivot allows the proximal end of the cutting tip to extend out of the plane.

The function of the tynes is to provide mechanical support for the blade. In many embodiments, the tynes are rigid. In some embodiments, however, the tynes are flexible. Now referring to FIG. 5, when the tynes are flexible, they can deflect or bow laterally to allow for increased blade flexion and conformance.

In some embodiments, and now referring to FIG. 2a, the tynes form an angle β therebetween of between about 30 degrees and about 60 degrees.

The blade is the active component of the instrument and performs the cutting of the cartilage material, preferably the intervertebral disc material. The cutting action of the blade is carried out by a sharp, beveled edge.

The flexibility of the blade allows it to conform to the surface. In some embodiments, and now referring to FIG. 2b, the shaft and tynes form a plane, and the flexible blade extends from the plane at an angle α of between about 30 degrees and about 60 degrees. This angled extension provides the blade with a more severe bite of the disc tissue (in comparison to a 90 degree angled extension) when the shaver is pulled proximally across the disc tissue.

In some embodiments, the flexible blade extends from the tynes in a first direction, thereby allowing the blade to be the only component of the shaving instrument that touches the disc tissue surface.

In some embodiments, the flexible blade is adjustable in the first direction. This adjustability allows the surgeon the freedom to select the depth of cut provided by the blade.

In some embodiments, and now referring to FIG. 2c, the blade curves between the tynes. This curve advantageously mimics the anatomical curve of the cartilage; increases the contact area therebetween; and provides for flexibility upon compression loading. In embodiments thereof, the blade forms a radius of between about 0.1 cm and about 2 cm.

The blade can be formed from any conventional biocompatible structural material. In some embodiments, the blade is metallic. In some embodiments, the blade is polymeric. In others, it is ceramic.

Figure 6A:
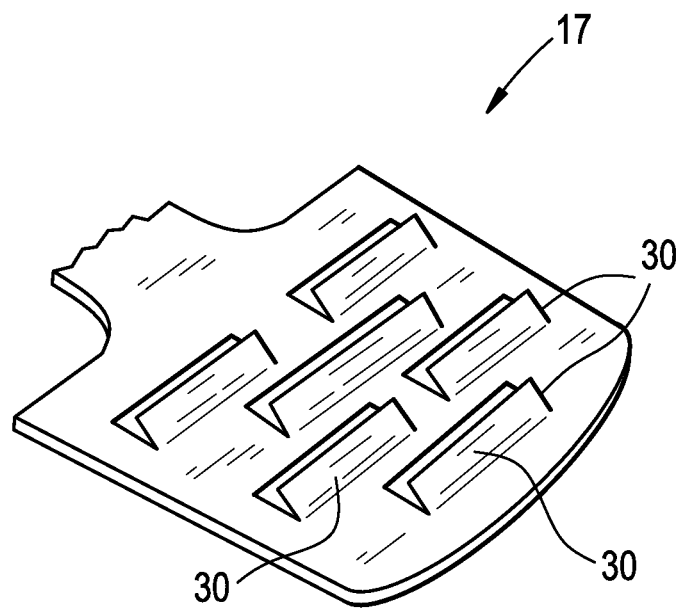
FIGS. 6A and 6B disclose an embodiment of the blade of the present invention having a plurality of cutting surfaces.
Figure 6B:
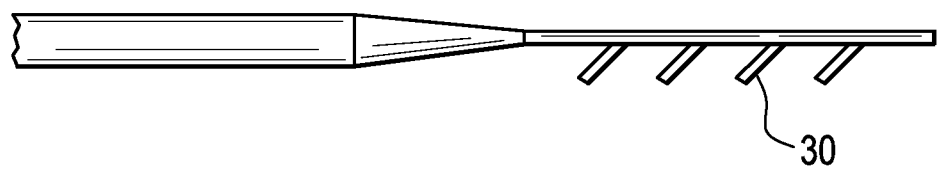

In some embodiments, and now referring to FIGS. 6A and 6B, the blade comprises a plurality of cutting surfaces 30. The plurality of cutting surfaces produces a more effective cut of the disc tissue.

In some embodiments, the blade can be modular to allow for its easy interchangeability.

In some embodiments, there is a support 31 connected to each of the distal end portions of the tynes. This support lies distal of the blade. The function of this component is to provide structural support to the blade during the shaving function. In some embodiments, the rigid support comprises an outer surface 33 having a convex shape. The convex shape has the advantage of providing a blunted entry tip shielding the blade from tissue not intended to be removed. The convex blade also allows for blade flexion and conformance to the vertebral body. In some embodiments, the support is rigid, while in others it is flexible. In some flexible support embodiments, the flexibility is imparted by relief grooves preferably disposed in the support orthogonal to the blade edge. In some embodiments, both the blade and its support combine to provide a flexible end portion of the cutting tip that flexes in response to the conventional level of force used by a spinal surgeon in shaving the cartilaginous tissue from an endplate of a disc space.

A component is considered "flexible" when it flexes under the typical compression force used by a spinal surgeon in the shaving of cartilaginous material from an endplate with a conventional curette. Preferably, the amount of flexing produced by the curette of the present invention causes the blade to conform to the underlying bony anatomy.

In some embodiments, the shaft of the present invention is flexible. In some embodiments, the tynes of the present invention are flexible. In some embodiments, the blade of the present invention is flexible. In some embodiments, the flexibility is imparted by relief grooves disposed in the component. In some embodiments, the flexibility is imparted by selecting a material of high inherent flexibility. In some embodiments, the flexibility is imparted by selecting a low material thickness.

In some embodiments, the instrument of the present invention is provided to the surgeon in a sterile form in a sealed package.

The curette of the present invention is adapted to cut soft tissue. Preferably, this soft tissue is present in a human joint. In some embodiments thereof, the joint is a functional spinal unit. In some embodiments, it is a knee joint. In some embodiments, it is a hip joint.

In one example of using the curette of the present invention, the surgeon will typically precut the disc annulus to create an entry window. The surgeon then inserts the distal end of the instrument into the disc space. The plane created by the shaft and tynes is preferably parallel to the endplates upon insertion. The surgeon then presses the cutting edge of the blade against the vertebral endplates and pulls proximally. As the shaver is so pressed and drawn, the disc nucleus pulposus, annulus and cartilaginous tissue are cut or excised from the vertebral endplates. The blade's flexibility allows for deflection at locations where excessive load is being incurred, thereby preventing excessive endplate damage. The shaver can be advanced further into the disc such that the contralateral aspects of the disc including the annulus are cut and excised. Following use, the instrument is withdrawn from the disc and any tissue that has accumulated within the shaver window (i.e., the area between the tynes and the blade) is removed. Shavers from a kit of various sizes, geometries and flexibilities can be used to customize the disc cleaning and control the amount of cartilaginous tissue excised from the endplate.

The surgeon can perform the shaving procedure from any access location of the disc, including posterior, lateral, anterior, antero-lateral, and postero-lateral.

In certain embodiments, these flexible curettes are used to prepare vertebral endplates associated with a non-parallel functional spinal unit (such as L5/S1) for the lateral insertion of a fusion cage.

Therefore, in accordance with the present invention, there is provided a method of preparing a vertebral endplate, comprising the steps of:
 a) removing an intervertebral disc to create a disc space and expose first and second vertebral endplates,
 b) inserting a curette of the present invention into the disc space, and
 c) proximally moving the shaver against at least one of the vertebral endplates to remove cartilage from the vertebral endplate.

In some embodiments, the shaver of the present invention has additional electrosurgical or ultrasonic components that provide electrosurgical or ultrasonic capabilities to enhance the effectiveness of the cutting action. In some embodiments, the electrosurgical component is a bipolar electrode component.

When a flexible material is selected as the material of construction for a component of the present invention, the flexible material is preferably selected from the group consisting of a metal and a polymer. In some embodiments, the polymer is selected from the group consisting of polyethersulfone, polyphenylsulfone, polyurethane, polyamides, polyimides, PEEK, polyethylene, polypropylene, and superelastic materials. When a rigid material is selected as the material of construction for a component of the present invention, the rigid material is preferably a metal and is more preferably selected from the group consisting of stainless steel, chromium cobalt, and titanium alloy. When the blade is flexible, it may be made of metal or plastic. When the tynes are flexible or rigid, they may be made of metal or plastic.

Figure 7:
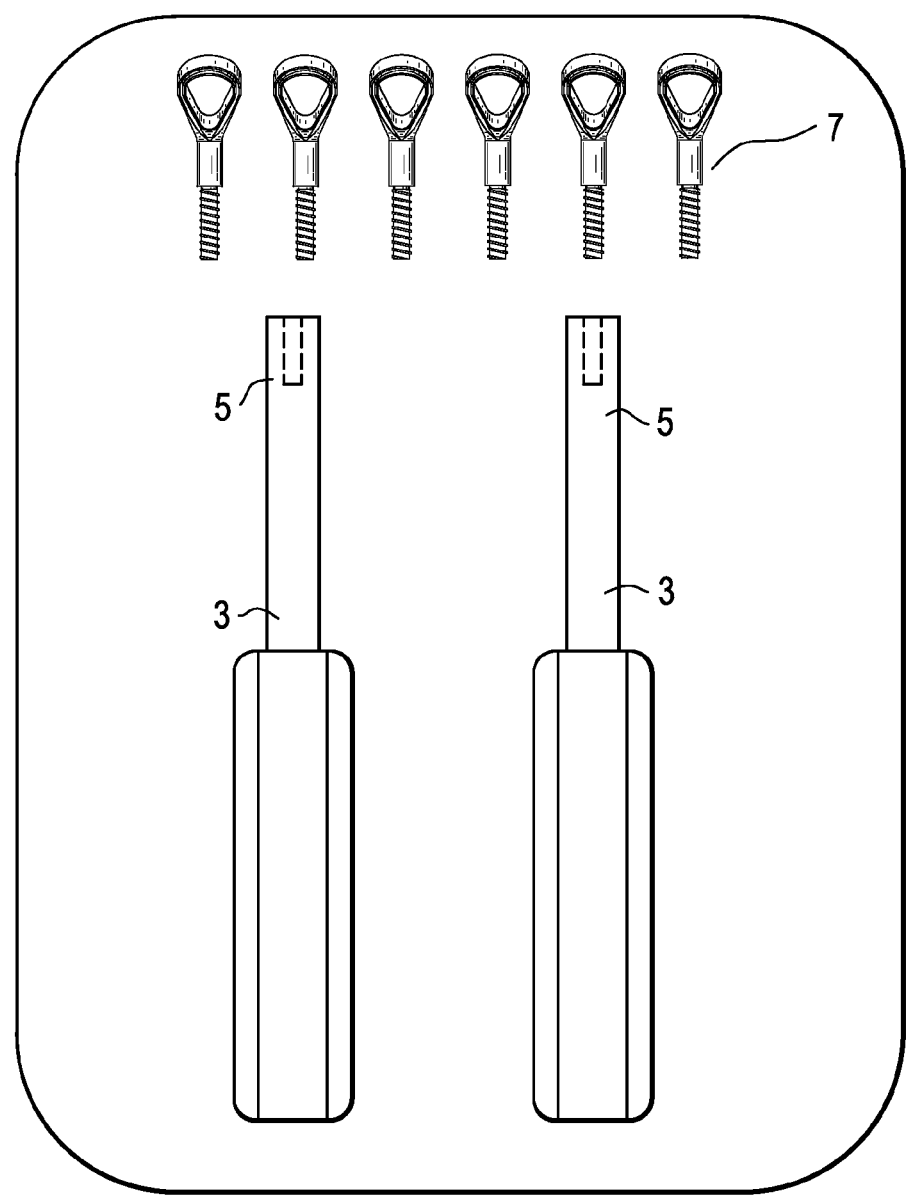
FIG. 7 discloses a pre-sterile kit of the present invention.

In some embodiments, and now referring to FIG. 7, there is provided a pre-sterile kit of a plurality of shavers of the present invention. The shavers in the kit may be of different sizes, different flexibilities, and/or different pivoting abilities. Some kits of the present invention may include a plurality of identical shavers. Some kits may include a standard shaft-with-handle component to which a plurality of modular cutting tips may be attached.

We claim:
1. An instrument for removing soft tissue, comprising:
 a) a shaft having a proximal end portion and a distal end portion,
 b) a cutting tip attached to the distal end portion of the shaft, the tip comprising:
  i) a proximal end portion adapted to attach to the shaft, and
  ii) a distal end portion comprising:
   first and second tynes extending distally from the proximal end portion of the cutting tip, each tyne having a distal end portion, and a flexible blade connected to each of the distal end portions of the tynes,
  wherein the blade is adapted to flex in response to a conventional level of force used by a spinal surgeon in shaving cartilaginous tissue from an endplate of a disc space,
  wherein the shaft and tynes to form a plane, and the flexible blade extends from the plane at an angle α of between 30 degrees and 60 degrees, and wherein the tynes form an angle β therebetween of between 30 degrees and 60 degrees.

2. The instrument of claim 1 wherein the proximal end portion of the shaft forms a handle.

3. The instrument of claim 1 wherein the distal end portion of the shaft and the proximal end portion of the cutting tip are integral.

4. The instrument of claim 1 wherein the distal end portion of the shaft and the proximal end portion of the cutting tip are modular.

5. The instrument of claim 1 further comprising a pin, wherein the distal end portion of the shaft has a first throughhole, the proximal end portion of the cutting tip has a second throughhole, and the pin passes through each throughhole.

6. The instrument of claim 1 wherein the distal end portion of the shaft and the proximal end portion of the cutting tip are removably mated.

7. The instrument of claim 1 wherein the cutting tip further comprises a pivot located between its proximal end portion and its distal end portion.

8. The instrument of claim 7 wherein the tynes form a plane, and the pivot allows the proximal end of the cutting tip to extend out of the plane.

9. The instrument of claim 1 wherein the tynes are rigid.

10. The instrument of claim 1 wherein the tynes are flexible.

11. The instrument of claim 1 wherein the flexible blade extends from the tynes in a first direction.

12. The instrument of claim 11 wherein the flexible blade is adjustable in the first direction.

13. The instrument of claim 1 wherein the blade curves between the tynes.

14. The instrument of claim 1 wherein the blade is metallic.

15. The instrument of claim 1 wherein the blade is polymeric.

16. The instrument of claim 1 wherein the blade comprises a plurality of cutting surfaces.

17. The instrument of claim 1 wherein the blade forms a radius of between 0.1 cm and 2 cm.

18. The instrument of claim 1 further comprising a support connected to each of the distal end portions of the tynes at a location distal of the flexible blade, wherein the support provides structural support for the blade.

19. The instrument of claim 18 wherein the support comprises an outer surface having a convex shape.

20. The instrument of claim 18 wherein both the blade and its support combine to provide a flexible end portion of the cutting tip that flexes in response to a conventional level of force used by a spinal surgeon in shaving cartilaginous tissue from an endplate of a disc space.

21. The instrument of claim 1 in a sterile form in a sealed package.

22. The instrument of claim 1 having an additional electrosurgical or ultrasonic component.

* * * * *